(12) United States Patent
Xia et al.

(10) Patent No.: US 9,790,782 B2
(45) Date of Patent: *Oct. 17, 2017

(54) IDENTIFICATION OF THERMAL CONDUCTIVITY PROPERTIES OF FORMATION FLUID

(71) Applicant: HALLIBURTON ENERGY SERVICES INC., Houston, TX (US)

(72) Inventors: Hua Xia, Huffman, TX (US); Li Gao, Katy, TX (US); Robert Atkinson, Conroe, TX (US); Christopher Michael Jones, Houston, TX (US)

(73) Assignee: HALLIBURTON ENERGY SERVICES INC., Houston, TX (US)

( * ) Notice: Subject to any disclaimer, the term of this patent is extended or adjusted under 35 U.S.C. 154(b) by 316 days.

This patent is subject to a terminal disclaimer.

(21) Appl. No.: 14/426,332

(22) PCT Filed: Mar. 10, 2014

(86) PCT No.: PCT/US2014/022817
§ 371 (c)(1),
(2) Date: Mar. 5, 2015

(87) PCT Pub. No.: WO2015/137915
PCT Pub. Date: Sep. 17, 2015

(65) Prior Publication Data
US 2016/0258279 A1    Sep. 8, 2016

(51) Int. Cl.
*E21B 47/06* (2012.01)
*E21B 49/08* (2006.01)
(Continued)

(52) U.S. Cl.
CPC ............ *E21B 47/065* (2013.01); *E21B 49/08* (2013.01); *E21B 49/081* (2013.01); *E21B 49/10* (2013.01);
(Continued)

(58) Field of Classification Search
CPC combination set(s) only.
See application file for complete search history.

(56) References Cited

U.S. PATENT DOCUMENTS

| | | |
|---|---|---|
| 3,807,227 A | 4/1974 | Smith |
| 3,864,969 A | 2/1975 | Smith |

(Continued)

FOREIGN PATENT DOCUMENTS

| | | |
|---|---|---|
| GB | 810892 | 3/1959 |
| JP | 58202863 | 11/1983 |

(Continued)

OTHER PUBLICATIONS

Chiasson, Andrew; "Thermal Response Testing of Geothermal Wells for Downhole Heat Exchanger Applications"; Jan. 30-Feb. 1, 2012.

(Continued)

*Primary Examiner* — Lisa Caputo
*Assistant Examiner* — Nasir U Ahmed
(74) *Attorney, Agent, or Firm* — Polsinelli (57) ABSTRACT

A downhole well fluid sensing device is disclosed for determining thermal conductivity of a formation fluid produced by a sampled subterranean well, the sensor package having an annulus shaped, elongate body defining a cylindrical fluid sampling space, the elongate body and the sampling space having a common longitudinal center axis. The elongate body has a fluid entrance port that provides well fluid ingress into the fluid sampling space and a fluid exit port that provides well fluid egress out of the fluid sampling space. A heat source is coupled to the elongate body and located along a portion of the fluid path, and the heat source inputs heat into sampled well fluid. Finally, temperature sensing devices located between the fluid entrance port and fluid exit port measure heat conducted to (Continued)

the sampled well fluid, wherein each of the temperature sensing devices is radially spaced from the heat source.

20 Claims, 11 Drawing Sheets

(51) Int. Cl.
*E21B 49/10* (2006.01)
*G01N 25/18* (2006.01)
*G01V 9/00* (2006.01)

(52) U.S. Cl.
CPC .............. *G01N 25/18* (2013.01); *G01V 9/005* (2013.01); *E21B 2049/085* (2013.01)

(56) References Cited

U.S. PATENT DOCUMENTS

| | | | |
|---|---|---|---|
| 3,938,383 A | 2/1976 | Sayer | |
| 4,343,181 A | 8/1982 | Poppendiek | |
| 4,575,260 A | 3/1986 | Young | |
| 4,575,261 A | 3/1986 | Berger et al. | |
| 4,848,147 A | 7/1989 | Bailey et al. | |
| 4,944,035 A | 7/1990 | Aagardl et al. | |
| 5,159,569 A | 10/1992 | Xu et al. | |
| 5,226,333 A | 7/1993 | Hess | |
| 5,251,479 A | 10/1993 | Siegfried et al. | |
| 5,348,394 A | 9/1994 | Hori et al. | |
| 5,610,331 A | 3/1997 | Georgi | |
| 5,988,875 A | 11/1999 | Gershfeld et al. | |
| 6,132,083 A | 10/2000 | Enala | |
| 6,497,279 B1 * | 12/2002 | Williams | E21B 36/04 166/250.01 |
| 6,877,332 B2 | 4/2005 | DiFoggio | |
| 7,086,484 B2 | 8/2006 | Smith | |
| 7,526,953 B2 | 5/2009 | Goodwin et al. | |
| 7,717,172 B2 * | 5/2010 | Sonne | E21B 43/24 166/264 |
| 7,804,296 B2 | 9/2010 | Flaum et al. | |
| 7,937,999 B2 | 5/2011 | Blanz et al. | |
| 8,122,951 B2 | 2/2012 | Fukuhara et al. | |
| 8,240,378 B2 | 8/2012 | Sonne et al. | |
| 8,453,732 B2 | 6/2013 | Sonne et al. | |
| 2005/0002435 A1 | 1/2005 | Hashimoto et al. | |
| 2007/0119244 A1 | 5/2007 | Goodwin et al. | |
| 2010/0006284 A1 * | 1/2010 | Sonne | E21B 47/10 166/264 |
| 2011/0272150 A1 | 11/2011 | Ives et al. | |

FOREIGN PATENT DOCUMENTS

| | | |
|---|---|---|
| WO | 2011044489 | 4/2011 |
| WO | 12023758 | 2/2012 |

OTHER PUBLICATIONS

GHC Bulletin, Andrew D. Chiasson, Geo-Heat Center, Oregon Institute of Technology, Klamath Falls, Oregon, May 2012.
Hashem, Mohamed et al.; "Wireline Formation Testers"; Uses Beyond Pressure and Fluid Samples—a Viable Replacement of Production Tests; https://www.onepetro.org/conference-paper/SPWLA-2002-XX; 2002.
Desbrandes, Robert; "Formation Evaluation using In-situ Measurements of Formation Thermal Properties"; vol. 32, No. 2; https://www.onepetro.org/journal-paper/SPWLA-1991-v32n2a6; Mar.-Apr. 1991; retrieved on Nov. 3, 2013.
Prensky, Stephen. Temperature Measurement in Boreholes: An Overview of Engineering and Scientific Applications; published on Dec. 31, 1992.
The International Search Report and Written Opinion dated Dec. 5, 2014; in corresponding PCT patent application No. PCT/US2014/022817.

* cited by examiner

FIG. 12 ated with an example embodiment;
IDENTIFICATION OF THERMAL CONDUCTIVITY PROPERTIES OF FORMATION FLUID

CROSS-REFERENCE TO RELATED APPLICATIONS

This application is a national stage entry of PCT/US14/22817 filed Mar. 10, 2014, said application is expressly incorporated herein in its entirety.

FIELD

The subject matter herein generally relates to a system and method of measuring formation fluid thermophysical properties, and more specifically to in-situ identification of thermal conductivity properties of downhole hydrocarbon fluid.

BACKGROUND

During petroleum production operations, the thermophysical properties, such as thermal conductivity, specific heat, and viscosity of the downhole hydrocarbon fluid often affect production efficiency and cost. High viscosity hydrocarbon fluid production may require the application of external heat to reduce the viscosity of the fluid and enable fluid transport from one place in the reservoir to the well location. Efficiency of production more or less depends upon the external heating power and thermal energy transport within a limited time interval. Higher thermally conductive hydrocarbon fluid can effectively transport the thermal energy further than low thermally conductive fluids. It is desirable to be able to measure thermal conductivity properties during wireline logging services and during production processes. The formation fluid thermal conductivity properties that are obtained can be used for wellbore completion, production efficiency control, and optimization.

The thermal conductivity properties of the downhole formation fluids varies with pressure, temperature, and chemical composition or molecular weight; the measurement of thermal conductivity can therefore be used to identify formation fluids. Downhole formation fluids at different geometric locations may also have different thermophysical properties regarding viscosity, density, thermal conductivity, specific heat capacity, and mass diffusion. Each of these properties can at least partially govern transportation and mobility of crude oils, including high viscosity crude oils, and can consequently impact the recovery process of the crude oils.

Reservoir hydrocarbon fluids may have similar thermal conductivity properties but different viscosity, density, compressibility, mass diffusivity, and specific heat capacity. Knowing thermal conductivity and other thermophysical properties of the hydrocarbon fluid can at least partially enable optimization of a well completion design and crude oil production processes. Presently, the thermal conductivity property of the reservoir or downhole hydrocarbon fluid is collected and analyzed in a surface laboratory with a PVT method, which may take days or even months. This PVT method tends to reduce the accuracy of any measurements due to the passage of time since collection, and environmental changes at the collection point(s) which can occur over time. In-situ detection of these thermophysical properties can improve accuracy of measurement, improve well completion design, crude oil production processes, and production efficiency.

BRIEF DESCRIPTION OF THE DRAWINGS

Implementations of the present technology will now be described, by way of example only, with reference to the attached figures, wherein.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

In the following description, terms such as "upper," "upward," "lower," "downward," "above," "below," "downhole," "uphole," "longitudinal," "lateral," and the like, as used herein, shall mean in relation to the bottom or furthest extent of, the surrounding wellbore even though the wellbore or portions of it may be deviated or horizontal. Correspondingly, the transverse, axial, lateral, longitudinal, radial, etc., orientations shall mean orientations relative to the orientation of the wellbore or tool. Additionally, the illustrated embodiments are depicted such that the orientation is such that the right-hand side is downhole compared to the left-hand side.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "outside" refers to a region that is beyond the outermost confines of a physical object. The term "inside" indicate that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder.

The term "radially" means substantially in a direction along a radius of the object, or having a directional component in a direction along a radius of the object, even if the object is not exactly circular or cylindrical. The term "axially" means substantially along a direction of the axis of the object. If not specified, the term axially is such that it refers to the longer axis of the object and can be described as "longitudinally." The term "temperature sensing device" means a device configured to sense, determine, measure or derive temperature; the term can include, but is not limited to, resistance temperature sensor, thermocouple and heat sensor. The term "reservoir description tool" means a device configurable to perform formation pressure testing and/or sampling. Formation pressure testing and/or sampling includes, but is not limited to, wireline formation pressure testing and/or sampling.

Figure 1:
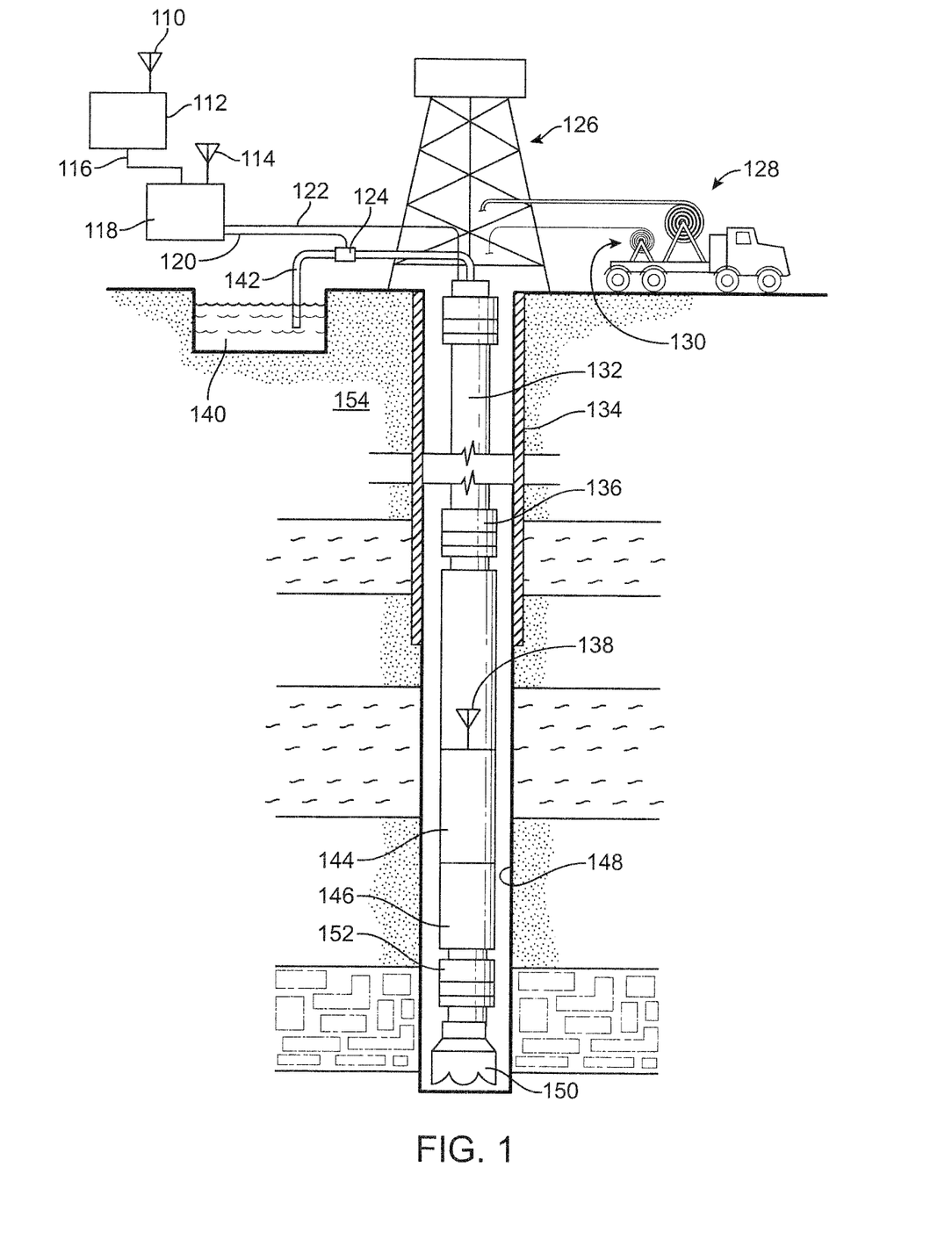
FIG. 1 is a perspective view of a subterranean well in accordance with an example embodiment.

The present disclosure is described in relation to a subterranean well that is depicted schematically in FIG. 1. A wellbore 148 is shown that has been drilled into the earth 154 using a drill bit 150. The drill bit 150 is located at the bottom, distal end of the drill string 132 and the bit 150 and drill string 132 are being advanced into the earth 154 by the drilling rig 126. The drilling rig 126 can be supported directly on land as shown or on an intermediate platform if at sea. For illustrative purposes, the top portion of the well bore 148 includes casing 134 that is typically at least partially comprised of cement and which defines and stabilizes the wellbore 148 after being drilled.

As shown in FIG. 1, the drill string 132 supports several components along its length. A sensor package 152 is shown for detecting conditions near the drill bit 150, conditions which can include such properties as formation fluid density, temperature and pressure, and azimuthal orientation of the drill bit 150 or string 132. In the case of directional drilling, measurement while drilling (MWD)/logging while drilling (LWD) procedures are supported both structurally and communicatively. Moreover, the sensor package 152 can detect characteristics of the formation surrounding the wellbore 148 proximate the sensor package 152 such as resistivity and porosity. Another sensor package 136 is shown within the cased portion of the well which can be similarly enabled to sense nearby characteristics and conditions of the drill string, formation fluid, casing and surrounding formation. Regardless of which conditions or characteristics are sensed, data indicative of those conditions and characteristics is either recorded downhole, for instance at the processor 144 for later download, or communicated to the surface via telemetry either by wire or wirelessly. If wirelessly, the downhole antenna 138 can be utilized to send data to a local processor 118, via topside antenna 114. There the data may be either processed or further transmitted along to a remote processor via wire 116 or wirelessly via antennae 114 and 110. The use of coiled tubing 128 and wireline 130 for downhole deployment is also schematically indicated and contemplated in the context of this disclosure. The possibility of an additional mode of communication is contemplated using drilling mud 140 that is pumped via conduit 142 to a downhole mud motor 146. Downhole, resistance to the incoming flow of mud is modulated to send backpressure pulses up to the surface for detection at sensor 124, and from which representative data is sent along communication channel 120 (wired or wirelessly) to one or more processors 118, 112 for recordation and/or processing.

Figure 2:
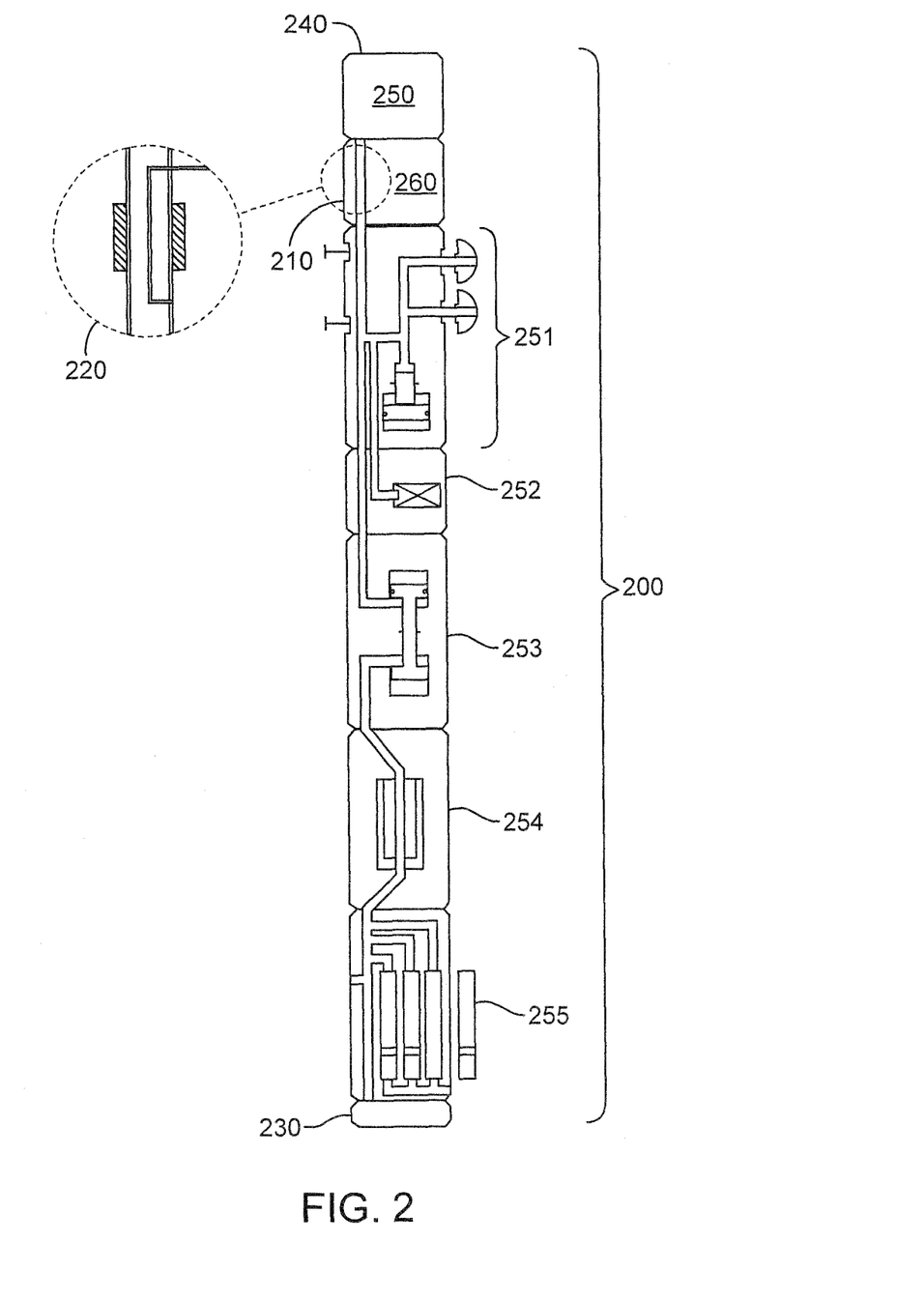
FIG. 2 is a front view of a reservoir description tool (RDT) module in accordance with an example embodiment.

FIG. 2 is an embodiment of the present disclosure that is part of the sensor package 152 of FIG. 1. As shown, module 200 can include a reservoir description tool (RDT) module with an in-situ formation fluid thermal identification (FTID) module 220 expanded from the indicated dashed circle 210, showing an example location on the RDT module 200. RDT modules can have many known components, such as a position tracking system (PTS) module 250, a dynamic positioning system (DPS) module 251, a temperature and pressure quartz gage sensor (QGS) module 252, a Flow-Control Pump-Out Section (FPS) module 253, a FLDS and magnetic resonance imaging (MRI) Lab module 254, and a mobile communications system (MCS) module 255 which are known to persons of ordinary skill in the art and therefore not described in detail. Finally, a first end 230 of RDT module 200 can be furthest downhole, closest to the bit, while a second end 240 is closest to the surface. Fluid can travel in the direction from the first end 230 to the second end 240.

Figure 3:
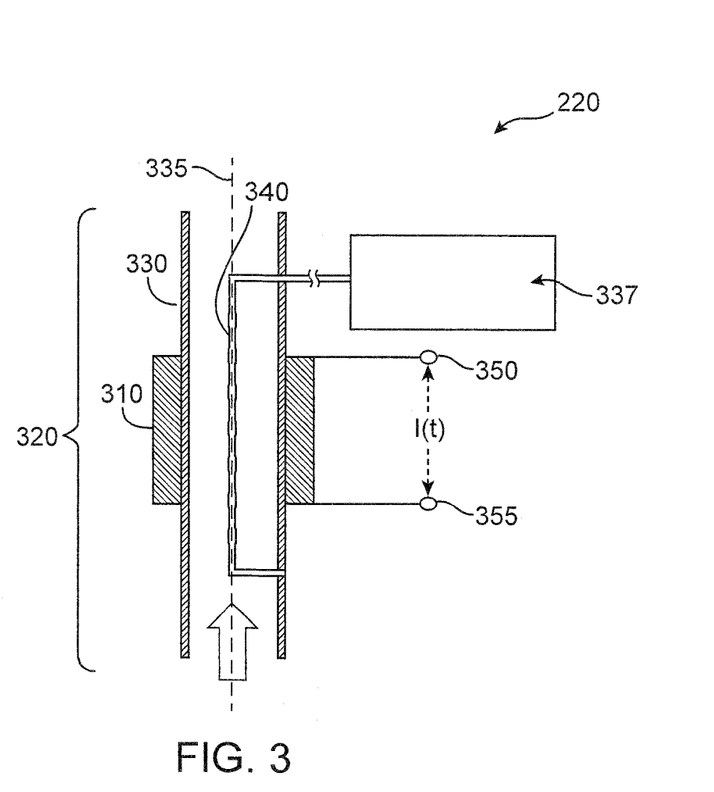
FIG. 3 is a partial view of a formation fluid thermal property sensing system in accordance with an example embodiment.

FIG. 3 schematically shows more detail about the fluid thermal identification (FTID) module 220 of FIG. 2. As shown, the FTID module 220 can be used to measure the thermal conductivity of the hydrocarbon fluid, the thermal conductivity of the formation fluid, or a combination of heat capacity and thermal conductivity of the formation fluid, and additional physical and chemical properties can be combined to make a robust downhole, in-situ analysis possible. The FTID module 220 can be isolated from the general surroundings to prevent contamination from outside sources, including unwanted heat transfer. The FTID module can be created using pipe or similar structure to form a sensor package and create a sampling space 320 that runs generally parallel with the overall RDT module 200. The sampling space 320 can be annulus shaped and can have an elongate body 330. The elongate body can be an elongate sensor package body. A pump (not shown) can be used to create a continuous flow of formation fluid through the sampling space 320. Heating element 310 can circumscribe the exterior of the sampling space and can heat the sampling space 320. The heating element 310 can be a heat pump. The change in temperature can be measured by temperature sensing devices 340 placed along the axis 335 in the direction of flow through the sampling space 320. As illustrated, temperature sensing devices 340 can be connected to a thermo sensor data acquisition system 337 which can collect or store or collect and store temperature data from temperature sensing device 340. Electricity can be supplied to the system through contacts 350 and 355, in this case providing power to the heat pump 310, thereby allowing the heat pump 310 to heat the formation fluid in sampling space 320.

Figure 4:
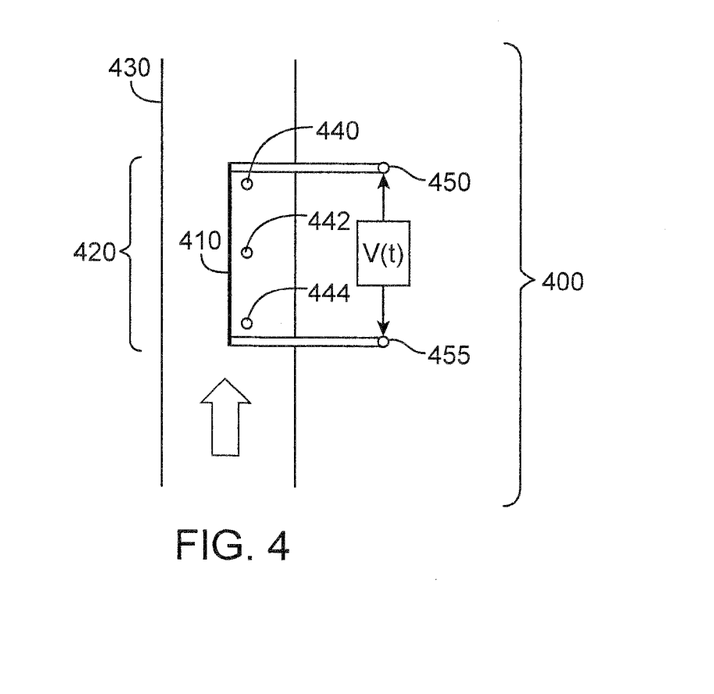
FIG. 4 is a partial view of a formation fluid thermal property sensing system that can measure a voltage drop in accordance with an example embodiment.

FIG. 4 shows another embodiment of the present disclosure for determining thermal conductivity characteristics of the hydrocarbon fluid. As shown, the measurement device 400 can be offset and isolated to assist in preventing contamination from outside sources. A pump (not shown) can cause a continuous flow of formation fluid through the sampling space 420 and body 430. The sampling space 420 can be annulus shaped and can have an elongate body 430. The elongate body 430 can be an elongate sensor package body. In this embodiment of the present disclosure, heating element 410 can add heat to the formation fluids while the formation fluids flow through the sampling space 420. Temperature sensing devices 440, 442, and 444 can measure the change in temperature of the formation fluids imparted by the heating element 410. While three temperature sensing devices are shown in this embodiment, the number of temperature sensing devices can be limited by their size and the size of the sampling space, as well as spacing efficiencies. Further, the location of both the heating element 410 and the temperature sensing devices can vary within the sampling space, as each can be moved so that they reside in the center of the sampling space or the temperature sensing devices can be moved outward towards the wall, depending on the measurements desired.

With regard to the sampling space generally, the isolated section typically can have a maximum length of 12 (twelve) inches, though the isolated section can have a different length. However, the length can vary above and below these lengths depending on the exact space constraints of individualized setups. The sampling space can further entail an outside pipe diameter of 1 (one) inch. Again, the outside diameter of the pipe can vary depending on the space constraints of the RDT module.

Heating elements or heat sources 310 and 410 can utilize any known heating method that works within the in-situ drilling environment. The heating elements or heat sources can be, for example, heat pumps, heating tape, heating wiring, resistance based, microwave-based, laser flashing or radiant heat based, coiled induction heat based, or a heat exchange mechanism. The heating elements or heat sources can be placed outside the sampling environment as shown in FIG. 3, in the center of the sampling environment as shown in FIG. 4, or anywhere in between, depending on the properties being measured. Further, the heating elements or heat sources can extend along the majority of the sampling space 320 or 420 or less than a majority of the sampling space 320 or 420. The heating elements or heat sources can be concentrically positioned about the longitudinal center axis of the sampling space. The heating elements or heat sources can also be positioned within the sampling space on the longitudinal center axis or at a distance from the longitudinal center axis. Still further, the heating elements or heat sources can be wound about or exteriorly circumscribe an exterior of the sampling space.

The thermal sensors (340 for example) or thermocouples (440 for example) can be any known temperature sensing device, examples of which are widely known and different temperature sensing devices have different sensitivities and properties that must be considered when choosing a specific model. Like the heating elements, the temperature sensing devices can be placed outside the sampling environment, in the center of the sampling environment as shown by FIG. 4, or anywhere in between, depending on the properties being measured. Specifically, the temperature sensing device can be located between the heat source and the fluid entrance port so that it can measure heat conducted upstream from the heat source. Another temperature sensing device can be located between the heat source and the fluid exit port to measure heat conveyed downstream from the heat source by the sampled well formation fluid flow. The temperature sensing devices can be aligned with one another and positioned parallel or substantially parallel to the longitudinal center axis of the elongate body and sampling space. In one or more embodiments, the temperature sensing devices are the arrayed thermocouple sensors, fiber distributed temperature sensors, arrayed fiber Bragg grating sensors, high-frequency temperature sensing devices, and/or arrayed resistivity temperature detectors.

When thermal properties are accurately known, more accurate measurements are enabled which facilitate improved well completion design and well production. Further, well drilling parameters can be changed for low-cost operation. Such parameters include the rate of advancement downhole, the force exerted on the bit, the speed of the bit, and other parameters recognizable by those persons of skill in the art. Accordingly, knowing thermal conductivity properties, and calculating these properties in-situ can enable improved drilling operation as well as production optimization. Finally, the thermal properties can be measured and stored at the RDT module 220, or transmitted, via a transmitter, to the surface for further calculations and actions based thereupon.

Figure 5:
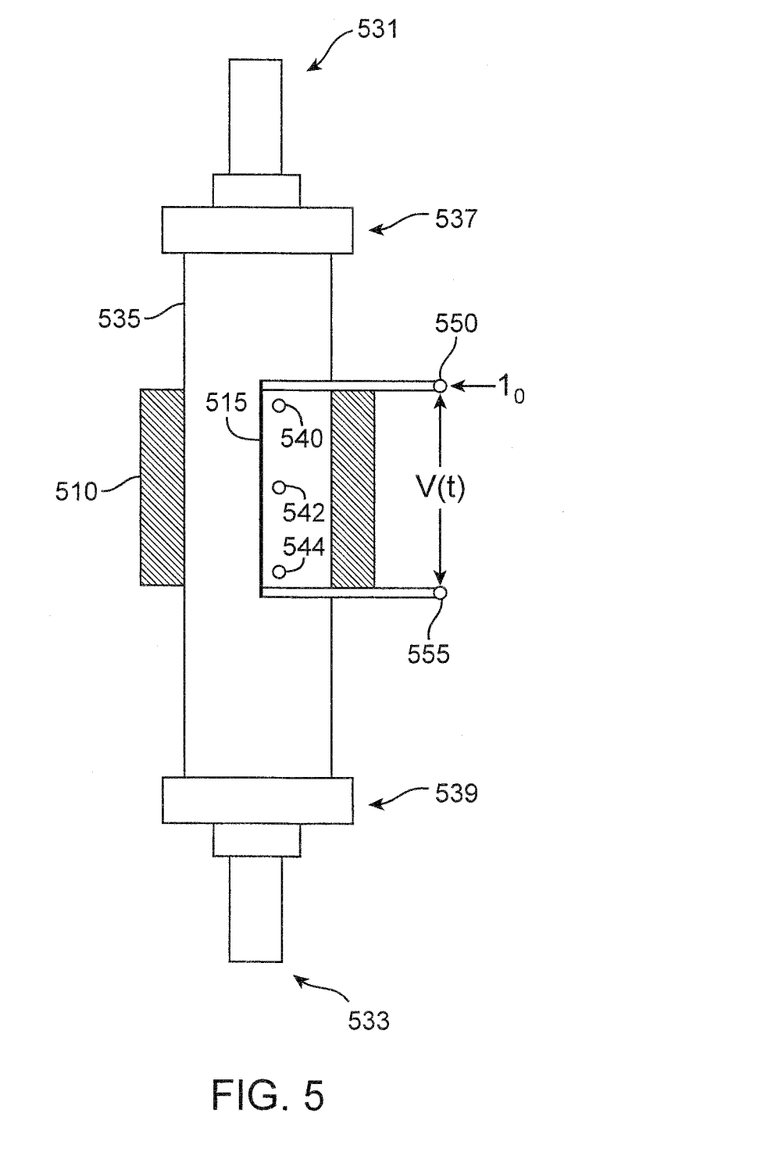
FIG. 5 is a sideview of a formation fluid thermal property sensing system that can measure a voltage drop in accordance with an example embodiment.

FIG. 5 shows a further example embodiment of the present disclosure having heating elements 510 and 515. In this case the entire isolation enclosure 535 is shown. The enclosure 535 can enable the internal flow and heat input to be isolated from other inputs beyond heating elements 510 and 515. The heating element 515 can be within the formation fluid and integrated with temperature sensing devices 540, 542, and 544. Formation fluid can enter through a first end, entrance port 533, and can travel from the bottom 539 of isolation enclosure 535 to the top 537 of isolation enclosure 535 and then exit via exit port 531. Heating element 515 can provide thermal energy via electrical resistance, with contacts 550 and 555 providing electricity to the heating element as well as heat pump 510, as desired. An implementation like the one shown in FIG. 5 can enable an operator to choose to use heating element 510, heating element 515, or a combination of both heating elements depending on the desired measurement(s) to be made.

Figure 6:
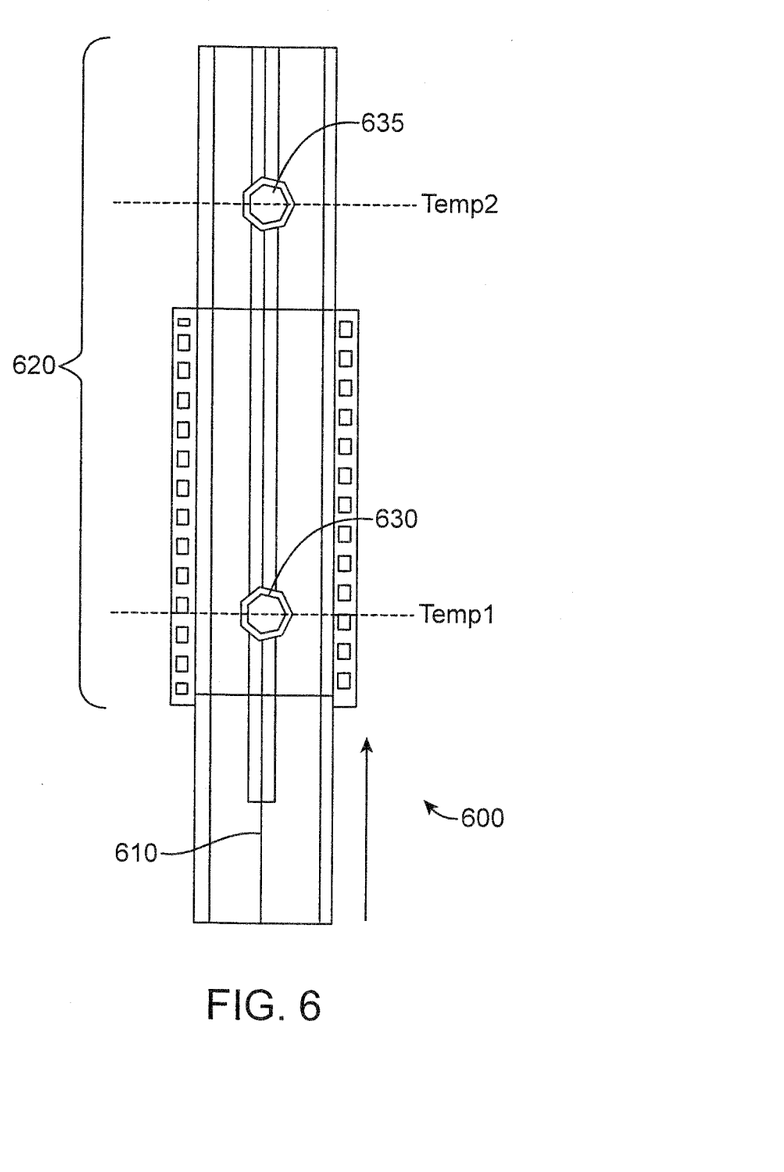
FIG. 6 is a partial view of a formation fluid thermal property sensing system that can measure temperature change in accordance with an example embodiment.

FIG. 6 shows another example embodiment of the present disclosure that can utilize heating element 610, which runs through the center of the sampling space 620, to heat the sampling space 620.

Figure 7A:
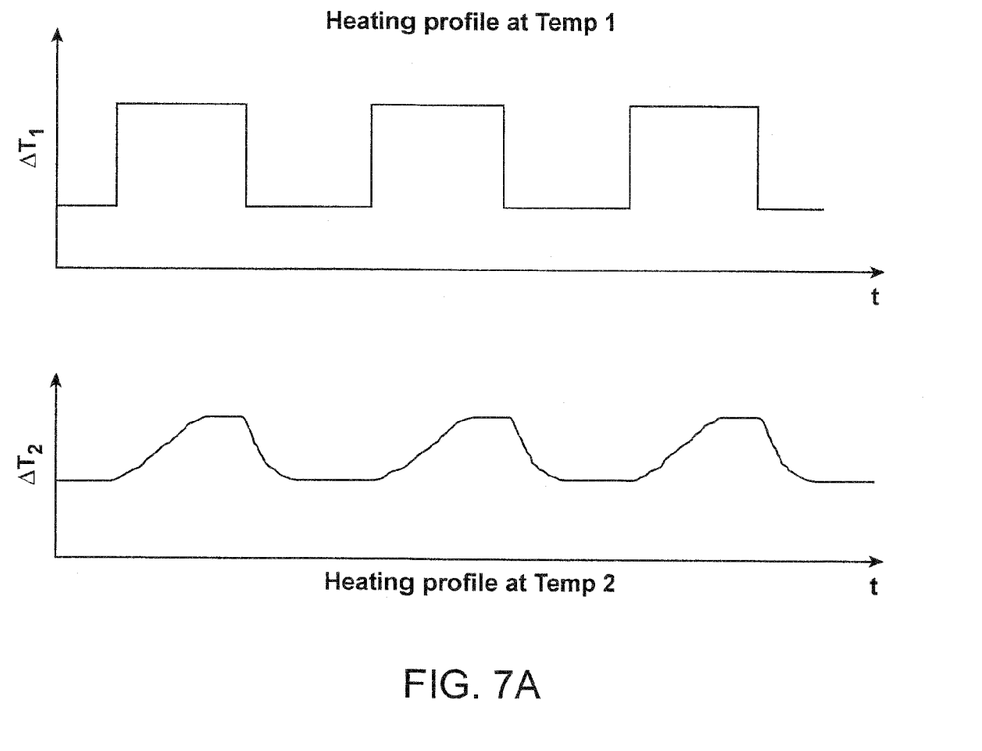
FIGS. 7A-7C are example graphs of temperature vs. time for high, medium, and low thermal conductive hydrocarbon fluids.
Figure 7B:
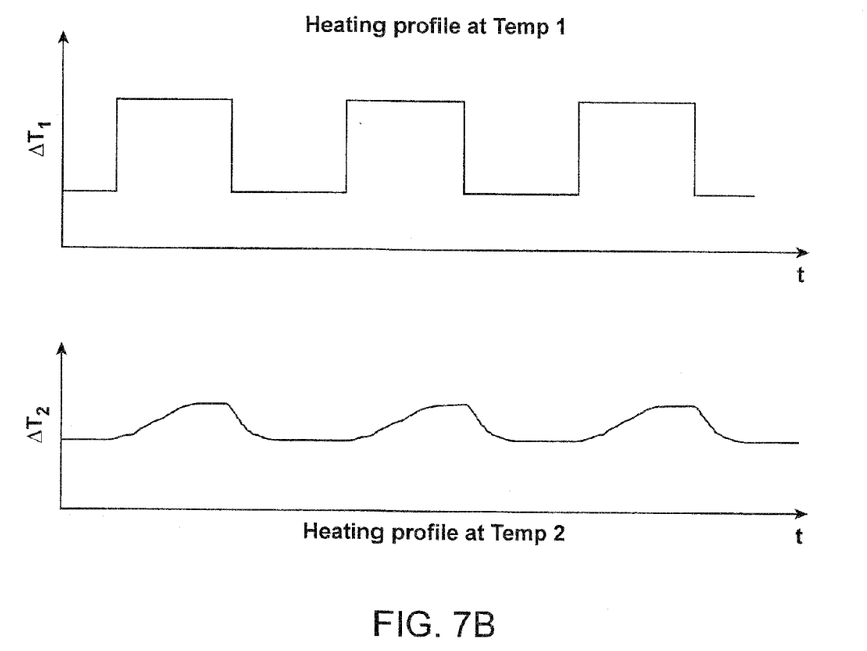
Figure 7C:
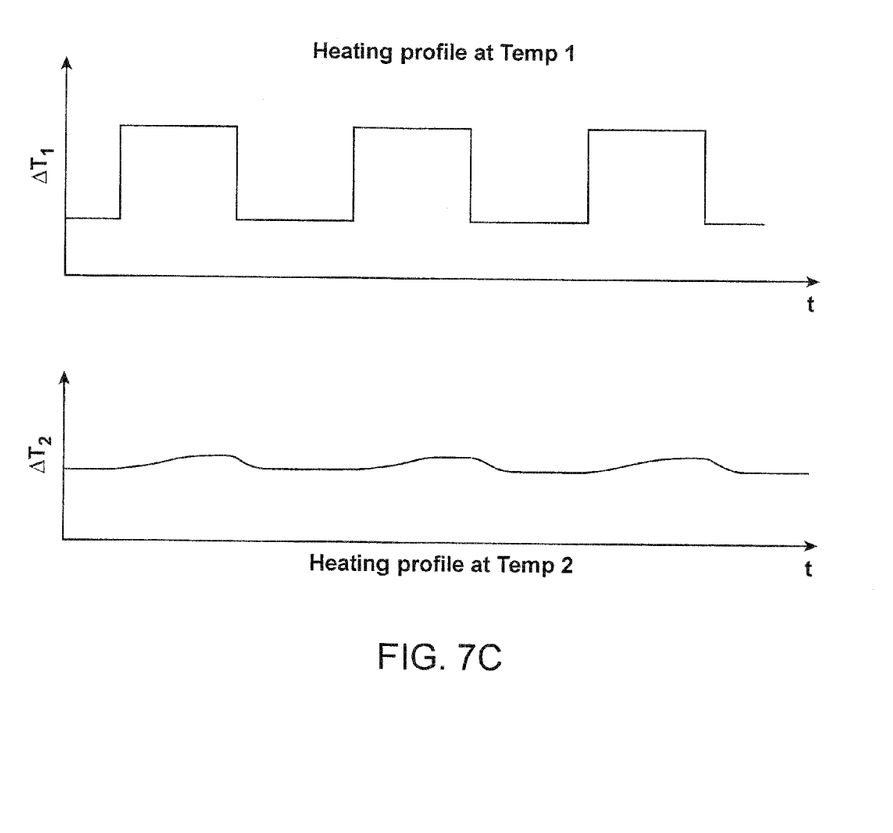

FIGS. 7A, 7B, and 7C are example graphs showing data obtained from the example embodiments of the present disclosure and can be directly collected from example embodiment 600. In FIG. 7A the formation fluid passing through the sampling space 620 can have a high thermal conductivity, k, which produces the graph shown in FIG. 7A. High k can be in the range from about 0.1 to about 200 W/m*K. FIG. 7B shows the temperature readings of a medium thermal conductive formation fluid flowing through sampling space 620. Medium k can be in the range from about 5 to about 50 W/m*K. Finally, FIG. 7C shows temperature results of a low k formation fluid flowing through sampling space 620. Low k can be in the range from about 0.1 to about 5 W/m*K. The ranges discussed herein are in no way limiting and the present disclosure can operate outside these ranges.

In at least one embodiment within this disclosure, the heating element can be made of any thermally conductive and electrically resistive material, such as metal or metal alloy. Suitable metals include, but are not limited to, platinum (Pt), Pt-alloys, tungsten (W), and W-alloys. A preferred heating element can be protected with an electric insulating protecting layer for its application in the electric conductive fluid environment. This protecting layer can be a polymeric material, such as, but not limited to, polytetrafluoroethylene (PTFE), polyimide (PI), polyetherketone (PEEK), ultra-high molecular weight polyethylene, and combinations thereof. In one or more embodiments, the protecting material can have a thickness of 0.01 micrometer to 20 micrometers. In one or more embodiments, the protecting polymer material such as polyethylene may have a thermal conductivity greater than 100 W/m*K.

In one or more embodiments, the thermal sensors described herein can be any device capable of detecting a change in fluid properties such as dynamic and steady temperatures and/or can be capable of detecting dynamic thermal response profile along the sensing array. Suitable thermal sensors can include thermocouple (TC) sensors, resistivity temperature detectors (RTD), platinum resistivity detectors (PRT), fiber Bragg grating-based sensors, and/or optical time domain reflectometer (OTDR)-based Brillouin distributed fiber temperature sensors with centimeter spatial resolution. In one or more embodiments, fiber sensors from Micron Optics or from OZ Optics can be used due to their small size and intrinsic insulating properties.

As shown in FIG. 6, two temperature sensing devices 630, 635 can be used to measure temperature at two separate locations in the sampling space 620. These temperatures are plotted on the Y-axis of FIGS. 7A, 7B, and 7C, each against time on the X-Axis. This results in FIG. 7A, the high k graph, indicating that it takes longer for the temperature at 630 to fall and longer for temperature at 635 to rise. The temperature rises at 635 for FIG. 7B, the medium k, and FIG. 7C, the low k formation fluids and are fairly similar at this resolution, with the medium k attaining a higher temperature and holding it longer. In FIG. 7C the temperature falls at 630 more sharply; in other words, quicker, for the low k of FIG. 7C than for the medium k shown in FIG. 7B.

After the fluid thermal conductivity property has been measured, it can be used to identify gas, water, and oil. It can also be used to identify drilling fluid (mud) and mud filtrate. Thermal conductivity can also be used to analyze multi-phase fluids and to analyze hydrocarbon gas composition. There is an established relationship between thermal conductivity and the heat capacity, diffusivity, and density of a hydrocarbon fluid. Finally, to avoid long-term fouling and/or scaling issues, the thermal cycles can undergo low to high temperature induced thermal stress to make the sensors self cleaning.

Figure 8:
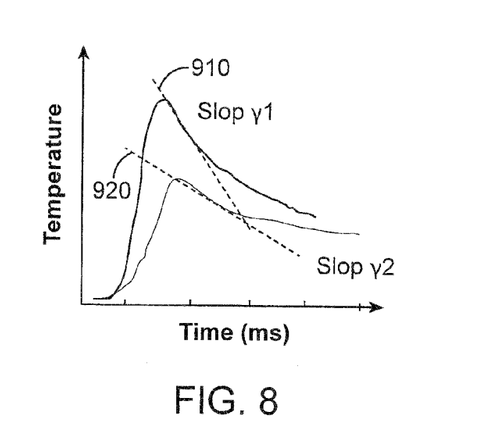
FIG. 8 is an example graph of temperature vs. time for transient thermal responses from Temp1 and Temp2 sensors.

FIG. 8 represents the results of an embodiment of the present disclosure that has a central heating wire, 410 like that of FIG. 4. The thermal properties of the formation fluid can be measured in-situ and the results are shown in FIG. 8. The graph is an introduced transient thermal dissipation profile analysis. In the embodiment used to create FIG. 8, the heating wire 410 can be integrated with the temperature sensing device array 440, 442, and 444. The current through the heating element 410 can be pulse modulated, initially the transient fluid temperature will sharply increase, then the temperature can begin to decay. The thermal conductivity of the fluids can be calculated based on the slope of the decay, indicated by dashed lines 910 and 920. The higher the fluid thermal conductivity, the quicker the measured fluid's temperature reaches to a maximum amplitude of $\Delta T_2$. The higher the fluid thermal conductivity, the greater the decay slope 910 and 920 can be. Either method, i.e., measuring $\Delta T$ or the decay slope, can be correlated to accurately determine the thermal conductivity.

Figure 11:
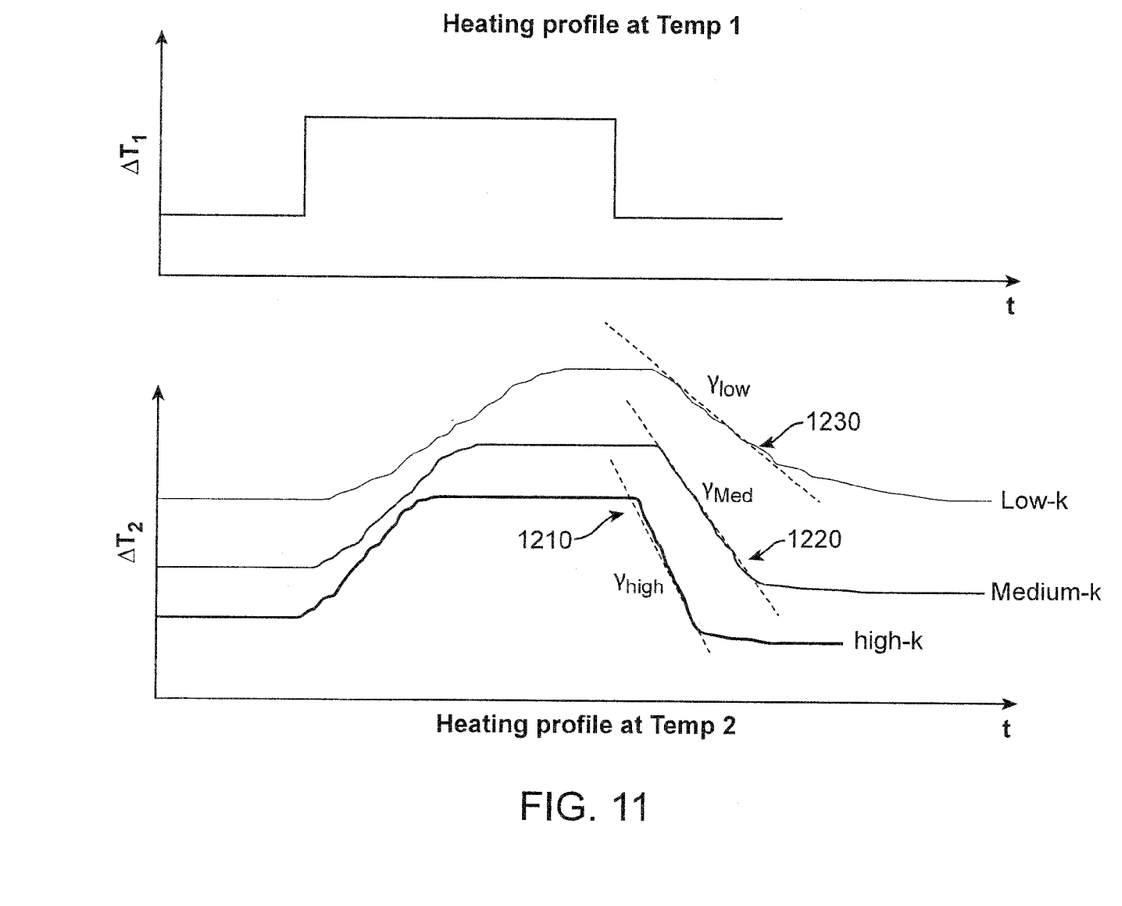
FIG. 11 is an example graph of transient thermal response from TEMP1 and Temp2 sensors under high and low thermal conductive hydrocarbon fluids.
Figure 12:
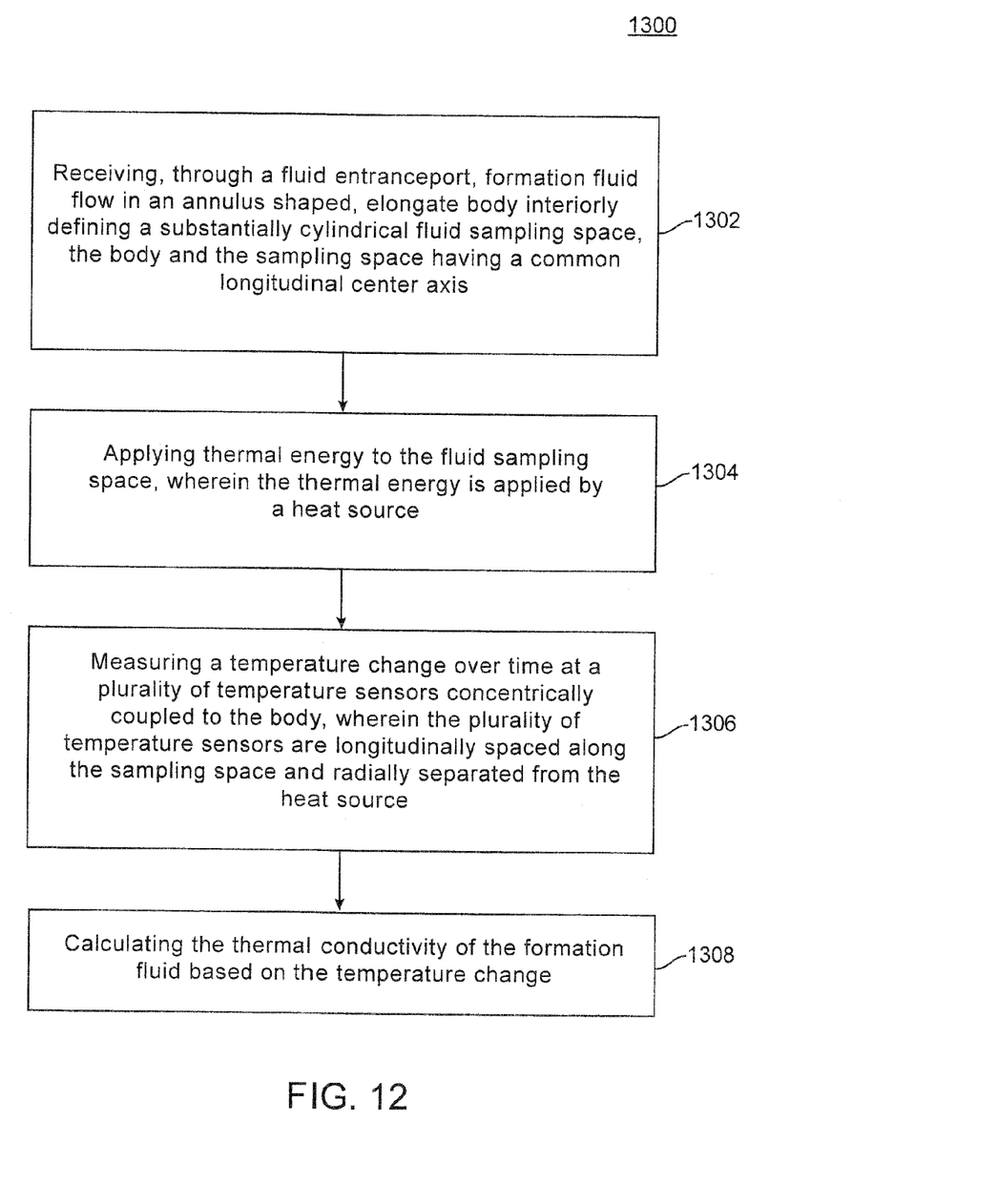
FIG. 12 is a flowchart illustrating a method for calculating thermal conductivity of hydrocarbon fluid.

FIG. 11 has normalized the measured transient thermal response curve from pulsed thermal excitation with a baseline temperature of the original fluid itself. The absolute temperature change $\Delta T(t)$ can be a function of time. In FIG. 12, this function is depending upon the thermal conductivity k. The slope of the transient thermal response decay, γ, is more or less related to the temperature drop of unit time interval. The higher of the fluid thermal conductivity, the fast the thermal profile decay, thereby the larger of its decay rate or slope.

Using a temperature sensing device array to detect transient thermal variation; the heating wire resistance is R(t), the voltage drop will be V(t)=I(0)*R(t); where R(t)=R(0)*(1+α$\Delta$T(t)), and transient voltage signal variation is $\Delta$V(t) =I(0)*R(0)*α*$\Delta$T(t). The theoretical analysis with one-dimensional heating wire thermodynamics can give:

$$\rho C p \frac{\partial T}{\partial t} = \lambda \frac{\partial^2 T}{\partial x^2} + G$$

where $\Delta T(x=0, t)=\zeta*t^{1/2}$, and leads to $\Delta V(t)=t^{1/2}/(\gamma \cdot K(t)+\beta)$. The thermal conductivity coefficient K(t) can be written as:

$$K(t) = \frac{1}{\gamma} * \left( \frac{\sqrt{t}}{\Delta V(t)} - \beta \right).$$

When measuring transient temperature variation, $\Delta T(t)$, the fluid thermal conductivity is determined by:

$$K(t) = \frac{1}{\gamma} * \left( \frac{\sqrt{t}}{I(0) \cdot R(0) \cdot \alpha \cdot \Delta T(t)} - \beta \right)$$

where the I(0) and R(0) and heating element thermal expansion coefficient α are known, such transient thermal detection can provide simple fluid thermal conductivity measurement in-situ for downhole fluid property analysis. β is reference value for calibration. One reliable and accurate method for determining K(t) is to use $\Delta T(t)=\Delta T(max)$, or t=t(max peak). In addition, the decay slope can be defined as γ=$\Delta T/\Delta t$, obtained after maximum transient amplitude data analysis. It should be pointed out that the measured effective thermal conductivity parameter k is a function of all hydrocarbon components that form formation fluid by $$k = \sum_{i=1}^{n} (x_i * k_i)$$

where $k_i$, i=1,2,3, . . . n, is thermal conductivity of each hydrocarbon component, and $x_i$ is fraction of i-th hydrocarbon composition in the formation fluid mixture.

Figure 9:
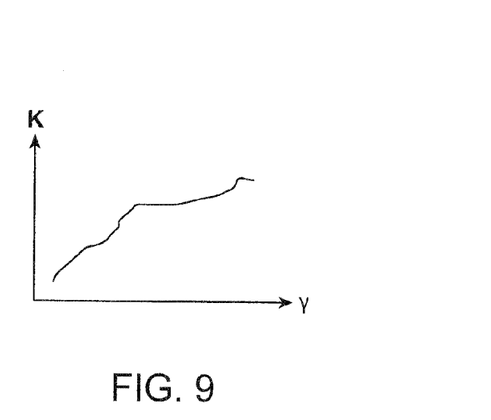
FIG. 9 is an example graph of K vs. γ.
Figure 10:
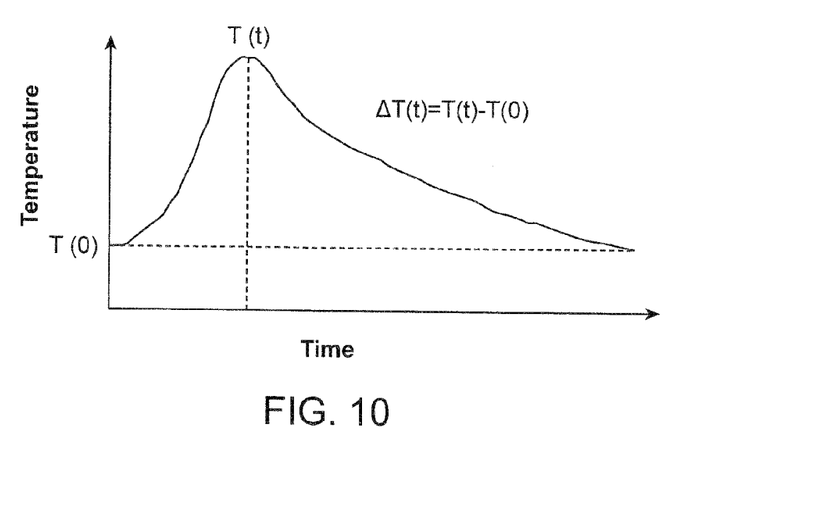
FIG. 10 is an example graph of normalized temperature vs. time for thermal conductivity analysis.

Based on the above described equations and calculations, the plots of K versus γ as shown in FIG. 9 can be created, as well as temperature versus time as shown in FIG. 10. This measured effective thermal conductivity property can be used to evaluate or identify water, oil, or gas, or a mixture of different hydrocarbon fluids. In another case, this effective thermal conductivity information can be combined with heat capacity and viscosity for formation fluid production optimization.

For heating wire inside the fluid, the pulsed heat energy transfers from heating element to fluid stream. When a pulsed heating wire has energized fluid that induces a temperature increase as given by $\Delta T$, the heat flow transfer is:

$$q = -k * \frac{\Delta T}{\Delta x} = h*(T - T_{n-1})$$

Where h is the convective heat transfer coefficient in W/m²K and thermal conductivity is in W/(mk). $T_{n-1}$ is the adjacent dynamic temperature along the package tube. Accordingly:

$$T(x) = T_{n\pm 1} + (T_n - T_{n\pm 1})*e^{-\left(\frac{h}{k}\right)x}$$

When T(x) is plotted, the graph of FIG. 11 can be produced. In this graph, the results measured for a fluid with a high thermal conductivity can be plotted as 1210, the results measured for a fluid with a medium thermal conductivity can be plotted as 1220, and the results measured for a fluid with low thermal conductivity can be plotted as 1230. The slope of each thermal response from a squared modulated heat energy excitation reflects speed of the heat energy dissipation to fluid. High conductive fluid will have a fast energy decay rate. A calibration transfer function will be used to interpret the corresponding thermal conductivity, k, versus the slope value.

Referring to FIG. 12, a flowchart is shown of a method for determining a thermal conductivity or other thermophysical parameters of formation fluid produced by a sampled subterranean well. The example method 1300 is provided by way of example, as there are a variety of ways to carry out the method. The method 1300 described below can be carried out using the components illustrated in FIGS. 3 and 4 by way of example, and various elements of these figures are referenced in explaining example method 1300. Each block shown in FIG. 12 represents one or more processes, methods, or subroutines, carried out in the example method 1300. The example method 1300 can begin at block 1302.

At block 1302 formation fluid is received through a fluid entrance port 533 into an annulus shaped, elongate body (330, 430) that defines a fluid sampling space (335, 435). The elongate body (330, 430) and the sampling space (335, 435) have a common longitudinal center axis. Then, method 1300 can proceed to block 1304, where thermal energy is applied to the fluid sampling space (335, 435) by a heat source (310, 410). After which method 1300 can proceed to block 1306 where the temperature within the sampling space is measured by temperature sensing devices (340, 440, 442, 444) concentrically coupled to the elongate body (330, 430) but radially separated from the heat source (310, 410). Finally, the method 1300 can proceed to block 1308 where the thermal conductivity is calculated for the formation fluid based on the measured temperature changes, and transient maximum response amplitude and decay rate.

At least one embodiment within this disclosure is a downhole well fluid sensing device wherein a plurality of temperature sensing devices (340, 440, 442, 444) are aligned, one with the others and positioned substantially parallel to the common longitudinal center axis of the elongate body (330, 430) and sampling space (320, 420). The temperature sensing devices could be arrayed thermocouple sensors; arrayed fiber Bragg grating sensors; optical time domain reflectometer (OTDR)-based Brillouin distributed fiber temperature sensors, or/and arrayed resistivity temperature detectors.

Further to the environmental context of a subterranean well depicted in FIG. 1, the downhole well fluid sensing device for determining thermal conductivity properties of formation fluid produced by a sampled subterranean well that is disclosed herein can be deployed on a drill string 132 as illustrated. Alternatively, the downhole fluid sensing device for determining thermal conductivity properties of formation fluid produced by a sampled subterranean well can be deployed on coiled tubing 128. The downhole fluid sensing device for determining thermal conductivity properties of formation fluid produced by a sampled subterranean well can also be deployed on wireline 130. Still further, the downhole fluid sensing device for determining thermal conductivity properties of formation fluid produced by a sampled subterranean well can be utilized in measurement while drilling (MWD) and logging while drilling (LWD) procedures.

The embodiments shown and described above are only examples. Many details are often found in the art such as the other features of a logging system or production cased well. Therefore, many such details are neither shown nor described. Even though numerous characteristics and advantages of the present sensing technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims.

What is claimed is:

1. A downhole fluid sensing device for determining thermal conductivity of a formation fluid produced by a sampled subterranean well, the device comprising:
    an annulus shaped elongated sensor package body interiorly defining a substantially cylindrical fluid sampling space, the elongated sensor package body and the sampling space having a common longitudinal center axis;
    a fluid entrance port providing a well fluid ingress into the fluid sampling space;
    a fluid exit port providing a well fluid egress out of the fluid sampling space;
    an upstream-to-downstream fluid flow path for a sampled well fluid extending from the fluid entrance port to the fluid exit port across the sampling space;
    a heat source coupled to the elongated sensor package body and located circumferentially around at least a portion of the fluid flow path between the fluid entrance port and the fluid exit port for inputting heat into the sampled well fluid; and
    a plurality of temperature sensing devices coupled to the elongated sensor package body and located between the fluid entrance port and fluid exit port for measuring heat conducted to the sampled well fluid, wherein each of the plurality of temperature sensing devices is radially spaced from the heat source and wherein the measurement is used to calculate the thermal conductivity of the formation fluid.

2. The downhole well fluid sensing device of claim 1, wherein the heat source is concentrically positioned about the longitudinal center axis of the sampling space.

3. The downhole well fluid sensing device of claim 2, wherein the heat source is positioned within the sampling space at a distance from the longitudinal center axis.

4. The downhole well fluid sensing device of claim 2, wherein the heat source is positioned outside the annulus shaped, elongate body at a distance from the longitudinal center axis.

5. The downhole well fluid sensing device of claim 4, wherein the heat source is a coiled heating element wound about an exterior of the annulus shaped, elongate body, and wherein the heat source is one or more of a resistive heating tape, an induction mechanism, a microwave mechanism, and a laser flush based heating mechanism.

6. The downhole well fluid sensing device of claim 2, wherein the heat source exteriorly circumscribes the annulus shaped, elongate body.

7. The downhole well fluid sensing device of claim 1, wherein the heat source comprises a plurality of heat inputs positioned at different locations about the elongate body.

8. The downhole well fluid sensing device of claim 1, wherein at least one of the plurality of temperature sensing devices is located between the heat source and the fluid entrance port for measuring heat conducted upstream from the heat source, and at least one of the plurality of temperature sensing devices is located between the heat source and the fluid exit port for measuring heat conveyed downstream from the heat source by sampled well fluid flow.

9. The downhole well fluid sensing device of claim 1, wherein the plurality of temperature sensing devices is aligned and positioned substantially parallel to the common longitudinal center axis of the elongate body and sampling space.

10. The downhole well fluid sensing device of claim 1, wherein the heat source extends along a majority of the elongate body.

11. A downhole fluid sensing device for determining heat capacity of a formation fluid produced by a sampled subterranean well, the device comprising:
an annulus shaped elongated sensor package body interiorly defining a substantially cylindrical fluid sampling space, the elongated sensor package body and the sampling space having a common longitudinal center axis;
a fluid entrance port providing a well fluid ingress into the fluid sampling space;
a fluid exit port providing a well fluid egress out of the fluid sampling space;
an upstream-to-downstream fluid flow path for a sampled well fluid extending from the fluid entrance port to the fluid exit port across the sampling space;
a heat source coupled to the elongated sensor package body and located is centrally positioned longitudinally within the sample space on a longitudinal center axis between the fluid entrance port and the fluid exit port for inputting heat into the sampled well fluid; and
a plurality of temperature sensing devices coupled to the elongated sensor package body and located between the fluid entrance port and fluid exit port for measuring heat conducted to the sampled well fluid, wherein each of the plurality of temperature sensing devices is radially spaced from the heat source and wherein the measurement is used to calculate the heat capacity of the formation fluid, wherein the heat source is centrally positioned longitudinally within the sample space on the longitudinal center axis.

12. A method for determining thermal conductivity of a formation fluid produced by a sampled subterranean well, the method comprising:
receiving, through a fluid entrance port, formation fluid flow in an annulus shaped, elongate body interiorly defining a substantially cylindrical fluid sampling space, the elongate body and the sampling space having a common longitudinal center axis;
applying thermal energy to the fluid sampling space, wherein the thermal energy is applied by a heat source coupled to the elongate body and located circumferentially around at least a portion of the fluid sampling space;
measuring a temperature change over time at a plurality of temperature sensing devices concentrically coupled to the elongate body, wherein the plurality of temperature sensing devices are longitudinally spaced along the sampling space and radially separated from the heat source; and
calculating the effective thermal conductivity of the formation fluid based on the temperature change profile and transient temperature response decay slope.

13. The method of determining the thermal conductivity of a formation fluid of claim 12, further comprising pumping the formation fluid, via a fluid exit port, out of the fluid sampling space, wherein a transient relative temperature amplitude is measured over time with a high-frequency temperature sensing device.

14. The method of determining the thermal conductivity of a formation fluid of claim 12, wherein applying thermal energy comprises applying a pulse-modulated thermal energy to the formation fluid along a portion of the substantially cylindrical fluid sampling space, wherein the pulse of thermal energy is applied by a heat source.

15. The method of determining the thermal conductivity of a formation fluid of claim 12, further comprising the step of:
altering, in-situ, a production optimization parameter based on the calculated thermal conductivity, wherein during time modulated external heat energy excitation, multi-point thermal sensors measure transient temperature response profiles and the thermal decay slope is used for thermal conductivity analyses.

16. The method of determining the thermal conductivity of a formation fluid of claim 12, further comprising the step of:
transmitting the calculated thermal conductivity by telemetry to a surface data processing system for use in altering a drilling or production parameter.

17. The method of determining the thermal conductivity of a formation fluid of claim 12, wherein the heat source is positioned within the sampling space at a distance from the longitudinal center axis.

18. The method of determining the thermal conductivity of a formation fluid of claim 12, wherein the heat source is positioned outside the annulus shaped, elongate body at a distance from the longitudinal center axis.

19. The method of determining the effective thermal conductivity of a formation fluid of claim 12, wherein the thermal energy is applied as a modulated energy pulse with electric current.

20. A method for determining thermal conductivity of a formation fluid produced by a sampled subterranean well, the method comprising:
receiving, through a fluid entrance port, formation fluid flow in an annulus shaped, elongate body interiorly defining a substantially cylindrical fluid sampling space, the elongate body and the sampling space having a common longitudinal center axis;
applying thermal energy to the fluid sampling space, wherein the thermal energy is applied by a heat source, the heat source centrally positioned within the sampling space on the longitudinal axis;

measuring a temperature change over time at a plurality of temperature sensing devices concentrically coupled to the elongate body, wherein the plurality of temperature sensing devices are longitudinally spaced along the sampling space and radially separated from the heat source; and calculating the effective thermal conductivity of the formation fluid based on the temperature change profile and transient temperature response decay slope.

\* \* \* \* \*